(12) United States Patent
Oikarinen et al.

(10) Patent No.: US 8,299,312 B2
(45) Date of Patent: Oct. 30, 2012

(54) PROCESS FOR DIMERIZING OLEFINS

(75) Inventors: Niilo Oikarinen, Porvoo (FI); Kari I. Keskinen, Helsinki (FI); Antti Pyhälahti, Helsinki (FI); Veli-Matti Purola, Hamari (FI)

(73) Assignee: Neste Oil Oyj, Espoo (FI)

( * ) Notice: Subject to any disclaimer, the term of this patent is extended or adjusted under 35 U.S.C. 154(b) by 1152 days.

(21) Appl. No.: 11/553,439

(22) Filed: Oct. 26, 2006

(65) Prior Publication Data
US 2007/0191662 A1    Aug. 16, 2007

Related U.S. Application Data

(60) Provisional application No. 60/731,372, filed on Oct. 28, 2005.

(51) Int. Cl.
*C07C 2/12* (2006.01)

(52) U.S. Cl. ........ 585/510; 585/502; 585/516; 585/520; 585/530; 585/532; 585/533

(58) Field of Classification Search .................. 585/510, 585/514, 532, 533, 520, 516, 502, 530
See application file for complete search history.

(56) References Cited

U.S. PATENT DOCUMENTS

| | | | |
|---|---|---|---|
| 3,325,465 A | 6/1967 | Jones | |
| 4,100,220 A | 7/1978 | Bowman | |
| 4,375,576 A | 3/1983 | Smith, Jr. | |
| 5,326,920 A * | 7/1994 | Ho et al. | 585/528 |
| 6,040,259 A * | 3/2000 | Mohr et al. | 502/67 |
| 2002/0131930 A1* | 9/2002 | Pinnavaia et al. | 423/702 |
| 2004/0138051 A1* | 7/2004 | Shan et al. | 502/60 |
| 2004/0181106 A1* | 9/2004 | Nurminen et al. | 585/533 |
| 2005/0043575 A1* | 2/2005 | Risch et al. | 585/324 |
| 2005/0222475 A1* | 10/2005 | Duplan et al. | 585/329 |
| 2005/0239634 A1* | 10/2005 | Ying et al. | 502/64 |

FOREIGN PATENT DOCUMENTS

| DE | 3542171 | 6/1987 |
|---|---|---|
| WO | WO 01/46095 | 6/2001 |

OTHER PUBLICATIONS

Yu, et al., "Preparation High Thermal Stability MCM-41 in the Low Surfactant/Silicon Molar Ratio Synthesis Systems," Materials Letters, 48 (2001), 112-116.*

Yu, et al., "Preparation of High Thermal Stability MCM-41 in the Low Surfactant/Silicon Molar Ratio Synthesis Systems," Materials Letters, 48 (2001), 112-116.*

(Continued)

*Primary Examiner* — In Suk Bullock
*Assistant Examiner* — Bradley Etherton
(74) *Attorney, Agent, or Firm* — Birch, Stewart, Kolasch & Birch, LLP

(57) ABSTRACT

A process for dimerizing olefins in the presence of a catalyst, a hydrocarbon feedstock containing $C_4$ to $C_6$ isoolefins is subjected to dimerization. The process comprises the steps of contacting the $C_4$ to $C_6$ isoolefins at conditions conducive to dimerization with a catalytic material comprising an acidic mesoporous molecular sieve, the catalytic material being thermally stable at a temperature of at least 900° C., and carrying out the contacting step essentially in the absence of butadiene and water in the feedstock. By means of the invention, the dimerization process can be operated over extended periods of time with prolonged maintenance intervals.

34 Claims, 3 Drawing Sheets

OTHER PUBLICATIONS

Li, et al., "Thermal and Hydrothermal Stabilities of the Alkali-Treated HZSM-5 Zeolites," J. Nat. Gas Chem., 17 (2008), 69-74.*
CRC Handbook of Chemistry and Physics, 90th ed., 2010 Internet Edition, D. R. Lide, ed., available on-line at http://www.hbcpnetbase.com.*

Karlsson, et al., "Composites of Micro- and Mesoporous Materials: Simultaneous Synthesis of MFI/MCM-41 like Phases by a Mixed Template Approach" in Microporous and Mesoporous Materials, 27 (1999) 181-192.*

* cited by examiner

Influence of dehydration on deactivation rate of catalyst

Regeneration of catalyst

PROCESS FOR DIMERIZING OLEFINS

This Nonprovisional application claims priority under 35 U.S.C. §119(e) on U.S. Provisional Application No. 60/731,372, filed on Oct. 28, 2005, the entire contents of which are hereby incorporated by reference.

BACKGROUND OF THE INVENTION

1. Field of the Invention

The present invention relates to the selective production of $C_6$-$C_{12}$ hydrocarbons useful as automotive fuel components. In particular, the present invention concerns a process for dimerizing lower, olefinic hydrocarbons in the presence of a catalyst under process conditions allowing for selective dimerization.

2. Description of Related Art

Light olefin dimers are useful intermediates in the manufacture of different products, like alcohols, ketones and carboxylic acids. Highly branched trimethylolefins and trimethylparaffins are useful as gasoline octane number enhancers.

Many processes for utilization of light olefins for the production of high quality transportation fuels are known. The Mobil Olefin to Gasoline and Distillate (MOGD) process converts propylene and butylene to olefinic distillate in high yields. The MOG or Mobil Olefins to Gasoline process is an extension of the MOGD. In MOG, the reaction conditions allow aromatics formation. Oligomerization of isobutene from $C_4$ olefins over zeolite catalysts has been disclosed in several US patents.

An essential feature of selective dimerization of light olefins is to prevent oligomerization, which is the successive reaction of dimerization. Selective dimerization of isobutene over trimerization and higher oligomerization is known from U.S. Pat. No. 3,325,465, DE Patent No. 3 542 171 and International Patent Application WO 01/46095. In U.S. Pat. No. 3,325,465, the use of nickel and cobalt ions in 13× zeolite is disclosed. In DE Patent No. 3 542 171, the selective dimerization of isobutene into trimethylpentene is made with bismuth or lead doped zeolite. In WO 01/46095, large pore zeolite Beta has been found to be selective for isobutene dimerization to the trimethylpentene in the presence of oxygenates. In addition, the reference teaches that dimerization can be carried out in the presence of an alcohol.

There are a few commercial dimerization processes. Institut Francais du Petrole (IFP) has developed a process for dimerization of light olefins (Dimersol). The Octol process, developed by UOP and Huls AG, produces linear octenes, which are the raw-materials of plastics softeners. Homogeneous catalysts are used in the processes.

Several processes are based on the use of ion exchange resins as dimerization catalysts. Such technical solutions are described, e.g., in U.S. Pat. Nos. 4,375,576 and 4,100,220. The known processes have many good properties but they all have the drawback of being totally dependent on oxygenate moderator, which improves the selectivity. This moderator has to be recycled and there is usually a significant amount of oxygen containing side products present in the dimerized product. When the reason to use dimerization is elimination of oxygenates from the components, these are highly undesired. Moreover, the oxygenates make hydrogenation of dimerized product more difficult.

All problems connected to oxygenates are solved if these compounds can be removed from the process altogether. Therefore, in an earlier patent application, WO 2004/080935, we have described a dimerization process, wherein an olefinic feedstock comprising $C_3$-$C_5$ isoolefins is contacted with a medium pore zeolite in order to dimerize the isoolefins into $C_6$-$C_{10}$ dimers. In the known process, dimerization is carried out in the presence of a heterogeneous zeolite catalyst. The catalyst can be any zeolite that is active in dimerization reactions. Such zeolites are exemplified by natural and synthetic medium pore size zeolites, such as ZSM-5, ferrierite, ZSM-22 and ZSM-23. These and similar catalysts having a pore size in the range of about 2 to 8 Å (0.2-0.8 nm), preferably 4 to 6 Å (0.4-0.6 nm), are active and selective for trimethyl olefins.

SUMMARY OF THE INVENTION

It is an object of the present invention to provide an alternative process for producing dimers useful, for example, as automotive fuels, in particular as gasoline components and as octane number enhancers.

The invention is based on the idea of dimerizing isoolefins and, potentially linear olefins, present in a $C_3$- to $C_6$-olefinic feed in liquid phase in a reaction sequence comprising at least one reaction zone and at least one separation zone. The reaction is carried out at conditions in which at least a part of the $C_4$- to $C_6$-isoolefins dimerizes. The separation zone is arranged after the reaction zone, and a circulation flow may be circulated from the separation zone back to the dimerization. The process is carried out essentially in the absence of polar compounds.

According to the invention, dimerization is performed out by contacting the isoolefines of the feedstock with an acidic mesoporous molecular sieve catalyst. In particular, the present invention utilizes a novel and active catalytic material having a mesoporous molecular sieve for example embedded with a zeolite structure.

Further, according to a preferred embodiment, the dimerization is performed essentially in the absence of butadiene, or more generally hydrocarbons containing multiple unsaturation ("multi-unsaturated hydrocarbons"), and water in the feedstock.

The invention also provides the use of a catalytic material having an acidic mesoporous molecular sieve, such as a mesoporous molecular sieve embedded with (i.e. in) a zeolite structure as an acid catalyst for dimerization of an olefinic feed containing unsaturated hydrocarbons, selected from the group consisting of isobutene, 1-butene, 2-butene, linear $C_5$-olefins and branched $C_5$-olefins.

More specifically, the process according to the present invention is mainly characterized by what is stated in the characterizing parts of claims 1 and 27.

Considerable advantages are achieved by means of the present invention. In conventional processes, selective dimerization rather than oligomerization is a desired but not easily achieved goal. When using the process of the present invention, high selectivity can be achieved in combination with high conversion rates.

A particular advantage of the present invention is that the process can be operated over extended periods of time with prolonged maintenance intervals, which reduces operation costs and makes production more efficient compared with previously used processes.

With conventional techniques, regeneration of the catalyst often poses a threat to continuous operation of the process. In the present invention, the catalyst can be regenerated continuously, during process operation. The easy regeneration gives a possibility to handle feeds containing nitrogen and sulphur impurities, along with conventional levels of multi-unsaturated hydrocarbons and water, which is a considerable advantage. By eliminating unsaturated hydrocarbons containing at least two double bonds or at least one triple bond, the regeneration interval even at industrial level can be extended considerably with considerable savings in costs as a result.

When an FCC feed, typically containing abundantly linear olefins, is used with conventional acid catalysts i.e. ion-exchange resins as catalyst, increasing concentrations of oxygenates are obtained. The hydrogenation of such compounds is difficult, if not impossible. By using catalysts of the present kind, oxygenate formation can be avoided and the time intervals for the operation can be extended.

Next the invention will be examined more closely with the aid of the following detailed description in which reference is made to the appended drawings.

DETAILED DESCRIPTION OF THE INVENTION

Definitions

Figure 1:
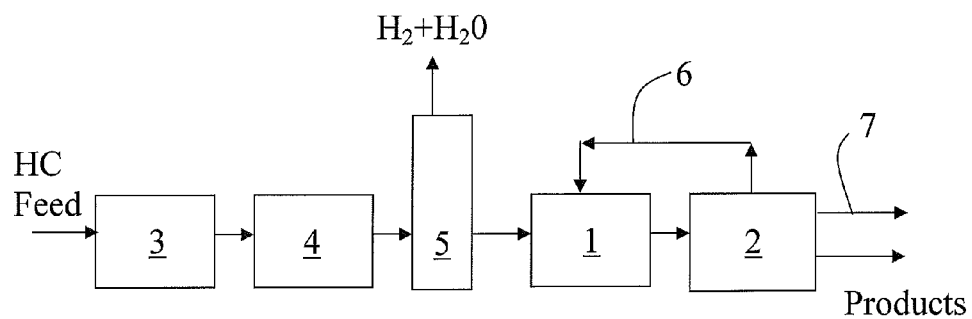
FIG. 1 depicts in a schematic fashion the process configuration of the basic technical solution of the invention.

For the purpose of the present invention a "reaction zone" denotes at least one, typically two or three, reactor(s). The reactor can be any continuous type reactor, in which a solid catalyst can be placed and that is capable of handling liquid reagents. Advantageously, the reactor is a simple tubular reactor, a packed bed reactor or a fluidized bed reactor. The reactor can be a tubular reactor with multiple pipes, wherein the pipes are filled with catalyst. Other possibilities include a reactive distillation unit with side reactors. The operating pressure of the reactors depends on the type of the reactor and on the composition of the feed, typically it is desired to keep the reaction mixture in liquid phase. In order to be able to regenerate the catalyst during reactor operation, it is often advantageous to use at least two reactors that can be regenerated in turn. Another advantageous mode of operation is to use a reactor, in which the catalyst can be regenerated continuously.

"Separation zone" designates a separation system that according to an embodiment comprises a distillation system comprising one or more distillation columns. The feed plate can be selected for each column to be most advantageous in view of the overall process. The distillation column can be any column suitable for distillation, such as a packed column, or one provided with valve, sieve or bubble-cap trays.

"Isooctene" and "di-isobutene" are both products of isobutene dimerization. Thus they can be used interchangeably to designate 2,4,4-trimethyl-1-pentene and 2,4,4-trimethyl-2-pentene or a mixture thereof.

"Isooctane" and "di-isobutane" comprise the corresponding hydrogenated paraffinic compounds.

"Effluent" contains the desired product of the dimerization reaction in the reaction zone. When only $C_3$-olefins, only $C_4$-olefins or only $C_5$-olefins are fed to the process, it is clear that the resulting product of the mutual reactions of the olefins yield dimers. However, when $C_3$-, $C_4$- and $C_5$-olefins are present in the feed, in addition to dimerization, also reactions between the different olefins may occur. The word "dimer" is also used for the reaction products in the specification for reasons of simplicity, but it is to be understood that when different lower olefins are present in the feed, the reaction mixture typically contains also some amount of the $C_9$-olefins.

According to a first preferred embodiment of the invention, the hydrocarbon feed containing isoolefins, such as isobutene, or linear olefins, such as butanes, or a mixture thereof, is contacted with an acid catalyst together in a essentially oxygenate-free reaction system comprising at least one reaction zone and at least one separation zone. The conditions are such that at least a part of the isoolefin is dimerized to isooctene. The flow from said reaction zone is introduced into a separation zone, where the main part of the dimerized reaction product is separated from the unreacted product. Advantageously, at least a part from the unreacted product is circulated from the separation zone back to the dimerization.

Importantly, the hydrocarbon feed is substantially free from multi-unsaturated hydrocarbons, such as 1,2- and 1,3-butadiene, propylene (acetylene) and isoprene, i.e. compounds containing at least two, potentially conjugated double bonds or at least one triple bond in contrast to the desired components of the feed, which contain one double bond (iso- or 1-olefines). By "substantially free from multi-unsaturated hydrocarbons", we mean a level clearly below the typical level of concentration of such compounds in for example, conventional industrial hydrocarbon feedstocks (refinery stream), such as FCC. In those refinery streams, there is 0.3 wt %, or even more—up to 1 wt % even—of butadienes. For the present invention, a maximum of 0.1 wt % or even below is desired, i.e. less than an upper limit of about 500 to 1000 ppm, in particular below about 100 ppm or even below about 50 ppm. Further, the dimerization feed should be substantially free from water. By "substantially free from water" we mean a concentration of 100 ppm or less. A more preferable content is less than 30 ppm and most preferably the concentration is 10 ppm or less when the feed is "substantially free" from water. As we will discuss more in detail in connection with Examples 2 to 5, both multi-unsaturated compounds and water have a strongly detrimental influence on the activity of the catalyst.

In order to free the feed from multi-unsaturated hydrocarbons, it is preferably subjected to selective hydrogenation, which can be carried out as known in the art, e.g. by contacting the feed with a suitable catalyst, e.g. a metal such as cobalt or nickel on alumina support or a noble metal (for example palladium or ruthenium), in the presence of hydrogen. By most of the technologies available the concentration of butadiene can be reduced to less than 100 ppm. Dehydration can be performed by activated aluminas and molecular sieves, as known in the art.

According to an embodiment of the invention, the hydrocarbon feed containing olefins is contacted with a specific kind of acid catalyst, namely a catalyst which comprises a mesoporous molecular sieve embedded in a zeolite, the catalytic material being thermally stable at a temperature of at least 900° C., at conditions in which at least a part of the olefins is dimerized. A description of such a composition and preparation of a particularly suitable catalyst type is given in FI Patent Application No. 20041675, the contents of which are herewith incorporated by reference. In case where the olefin feed comprises $C_3$- to $C_6$-olefins, also reactions between different olefins occur, thus forming higher (meaning up to $C_{12}$)-olefins. The effluent from the reaction zone is introduced into a separation zone, where the main part of the dimerized reaction product is separated to form a first product containing unreacted hydrocarbons and a second product containing the dimerized olefins.

The feed of the process according to the present invention is a hydrocarbon mixture containing olefins. The feed comprises olefins to be dimerized in a concentration of at least 10 wt-%, preferably at least approximately 20 wt-% of the total weight of the feedstock. As already described, the olefins are selected from the group of propylene, linear 1- or 2-butene, isobutene and linear or branched $C_5$-olefins. Alternatively, the feed can comprise a mixture of any or every of the olefins listed above. Typically, the feed comprises dimerizable components: $C_4$-olefins, preferably isobutene, whereby isooctene is produced, or $C_5$-olefins, whereby substituted $C_{1-10}$-olefins are produced. It is clear that both $C_4$- and $C_5$-olefins can be present in the feed, whereby a great variety of products is produced. The composition of the product flow is discussed later. Generally, the feed can contain olefins in the range of $C_3$ to $C_6$ olefines, although $C_4$ and $C_5$ olefins, in particular $C_4$ and $C_5$ isoolefins, are most interesting.

According to the first preferred embodiment, in which $C_4$-hydrocarbons are dimerized, the hydrocarbon mixture in the feed comprises at least 10 wt-%, preferably at least approximately 15 wt-% isobutene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40-60 wt-% of isobutene and 60-40 wt-% isobutane, usually there is 5-20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$-, $C_5$- and heavier hydrocarbons altogether.

The feed for producing isooctene can also be selected from the group containing $C_4$-fractions of FCC, TCC, DCC and RCC or from the $C_4$-fraction after the removal of butadiene, also called Raffinate 1 of an ethylene unit. Of these, FCC, RCC, TCC and Raffinate 1 are preferred, since the hydrocarbon fractions can be used as such, possibly after removing the heavier ($C_{8+}$) fractions. Raffinate 1 is typically composed of approximately 50 wt-% isobutene, approximately 25 wt-% linear butenes and approximately 25 wt-% paraffins. The product from the FCC is typically composed of 10-50, in particular 10-30 wt-% isobutene, 20-70 wt-% 1- and 2-butene and approximately 5-40 wt-% butane. As an example of a typical FCC-mixture, the following can be presented: approximately 17 wt-% isobutene, approximately 17 wt-% 1-butene, approximately 33 wt-% 2-butene and approximately 33 wt-% butane, and others.

Also isobutene prepared from chemicals can be used as feed.

According to another preferred embodiment of the invention, the olefins present in the olefinic feedstock are selected from the group of linear and branched $C_5$-olefins, such as linear pentene, 2-methyl-1-butene, 2-methyl-2-butene, 3-methyl-1-butene, and mixtures thereof.

According to an embodiment of the invention, the feedstock comprises aromatic hydrocarbons, paraffins and mixtures of these.

If the present invention is used for converting linear butenes, the linear butenes are preferably selectively isomerized to 2-butene as completely as possible. In this case, it is preferable to add a separate side reactor circulation to the process configuration. The temperature in this reactor is preferably higher than in the prereactor or circulation reactor in order to increase the conversion of dimerization.

FCC and corresponding hydrocarbon flows are suitable to use, e.g., in cases where the conventional MTBE unit is used to produce a product mixture comprising isooctene and MTBE.

According to the second preferred embodiment of the invention, in which $C_5$-olefins are dimerized, the feed comprises olefins selected from the group of linear and branched $C_5$-olefins, or a mixture thereof. Thus, the olefins typically present in the feed comprise linear pentene, 2-methyl-1-butene, 2-methyl-2-butene, 3-methyl-1-butene. Also some amounts of $C_6$-olefins, typically at least 5 wt-% can be present in the feed.

Typically, the feed in the second preferred embodiment is FCC gasoline, light FCC gasoline, pyrolysis-$C_5$-gasoline, TCC gasoline, RCC gasoline and Coker gasoline, typically the $C_5$-fraction of FCC gasoline. The feed can comprise also some $C_6$-olefins. Advantageously, the FCC fraction is fractionated to obtain as pure $C_5$-olefin fraction as possible where other $C_5$-hydrocarbons are present in less than 15 wt-%, preferably less than 5 wt-%. It is possible to use a fraction comprising also $C_6$-olefins. Typically, the feed then comprises 20 to 60 wt-%, in particular 30 to 50 wt-% $C_5$-olefins, 10 to 30 wt-%, in particular 15 to 25 wt-% $C_6$-olefins and 15 wt-% or less paraffinic hydrocarbons pentanes.

According to the third preferred embodiment, the feed comprises both $C_4$- and $C_5$-olefins. In this case, the feed is typically selected from the group comprising FCC, TCC, DCC and RCC or from the $C_4$-fraction after the removal of butadiene, also called Raffinate 1 of an ethylene unit, FCC gasoline, light FCC gasoline, pyrolysis-$C_5$-gasoline, TCC gasoline, RCC gasoline and Coker gasoline. A fraction readily available comprises $C_4$ and $C_5$ fractions from FCC. Advantageously, a fraction comprising at least 10 wt-%, preferably at least 15 wt-% $C_4$-olefins and at least 10 wt-%, preferably at least 15 wt-% $C_5$-olefins is used. Typically the amounts of $C_4$-olefins and $C_5$-olefins are approximately equal, although a slight dominance of $C_4$-olefins in the fraction is also usual.

According to the first preferred embodiment, $C_4$-olefins are dimerized. The compositions of the feed have already been discussed, and product compositions then are as follows:

When mainly dimers of isobutene are produced, they are typically present in the product flow in a concentration of at least 85 wt-%, preferably at least 90 wt-%. Other components typically present in the product flow are trimers of isobutene, 15 wt-% or less, preferably 10 wt-% or less, tetramers of isobutene in less than 0.2 wt-% and other hydrocarbons in less than 1 wt-%, preferably less than 0.1 wt-%.

Regardless of the aimed product composition most (65-100 wt-%, typically 85-100 wt-%, preferably 95-100 wt-%) of the dimers produced by the process are 2,4,4-trimethyl pentenes. When the product stream is hydrogenated, a mixture comprising isooctane is obtained. The fraction of other trimethyl pentanes (e.g. 2,3,4-trimethyl pentane) as well as the fraction of dimethyl hexanes in the mixture remains extremely small. Thus the octane number (RON) of the fuel component is high, typically at least 95, preferably approximately 98-100.

According to the second preferred embodiment, dimers of $C_5$-olefins are produced. The product is typically as follows:

At least 65 wt-%, preferably at least 70 wt-%, $C_5$-dimers, 5-32 wt-%, preferably 5-29 wt-% olefin trimers, less than 1 wt-%, preferably less than 0.5 wt-% olefin tetramers. Because no oxygenate is fed to the process, the amount of oxygenates in the process and in the final product is very small. When the composition is hydrogenated, a composition useful as a fuel component is obtained.

According to the third embodiment, dimers of both $C_4$- and $C_5$-olefins are produced. In addition also $C_4$- and $C_5$-olefins react and form Cg-olefins. The product composition then comprises at least 65 wt-%, preferably at least 70 wt-%, $C_5$-dimers, $C_4$-dimers and $C_9$-olefins, 5-32 wt-%, preferably 5-28.5 wt-% olefin trimers, less than 1 wt-%, preferably less than 0.5 wt-% olefin tetramers. When the composition is hydrogenated, a composition useful as a fuel component is obtained.

Regardless of the aimed product composition most (50-100 wt-%, typically 60-100 wt-%, preferably 90-100 wt-%) of the dimers and $C_9$-olefins produced by the process are isooctene, tetramethylpentenes and trimethylhexenes. When the product stream is hydrogenated, a mixture comprising corresponding hydrogenated hydrocarbons is obtained. The relative abundance of individual components varies depending on the ratio of the reactive $C_4$- and $C_5$-components in the feed. When the product stream is hydrogenated, a mixture comprising isooctane, tetramethylpentanes and trimethylhexanes is obtained. Thus the octane number (RON) of the fuel component is high, typically at least 95, preferably approximately 98-100.

The dimer fraction of the reaction product for a feed comprising (among other, less reactive compounds) both $C_4$- and $C_5$-isoolefins (typically in a ratio of 40:60 to 60:40, in particular about 45:55) includes 20-30 wt-%, in particular 25-28 wt-%, trimethylpentenes, 20-30 wt-%, in particular 20-25 wt-%, tetramethylpentenes and trimethylhexenes, 4-8 wt-%, in particular 5-6 wt-%, tetramethylhexenes, and 2-5 wt-%, in particular 3-4 wt-%, trimethylheptenes. The rest of the dimer product comprises or even consists of less branched olefins.

The product has a vapour pressure of 10-20 kPa (Reid) and a distillation point (90 vol-%, ASTM D86) is equal or less than 180° C.

A part of the first reaction product is typically circulated from the separation zone back to the reaction zone. It is to be understood that although the following description refers to a sideflow in the singular tense, which is the typical configuration, it is also possible to withdraw two or more sideflows and circulate all those flows back to dimerization.

According to an advantageous embodiment, the reaction zone comprises two reactors in parallel. The feed comprising fresh olefinic feed and recycled first product may be fed to one of the reactors, and the second reactor can be recovered simultaneously. The effluent from the reaction zone is introduced into a separation zone, where the main part of the dimerized reaction product is separated to form a first product containing unreacted hydrocarbons and a second product containing the dimerized olefins.

The selectivity of the dimerization reaction in a process according to our invention is high. According to an embodiment, the selectivity of dimerized olefins, expressed as the ratio of the molar amount of dimeric compounds to the total molar amount of converted olefins, is in excess of 0.8, in particular in excess of 0.9.

According to the invention, an acid catalyst is used. It has now been found that the problems relating to zeolite catalysts and mesoporous catalysts according to the state of the art can be avoided or at least significantly decreased by using a novel catalytic material, which is a mesoporous molecular sieve embedded with e.g. a zeolite, having high mechanical, thermal and hydrothermal stability. The novel mesoporous molecular sieve embedded in a zeolite is thermally stable at temperatures of at least 900° C. in the presence of air.

Therefore, the present invention uses a group of novel mesoporous molecular sieves, which are mechanically, thermally and hydrothermally stable. These materials are very well reproducible as can be seen in the examples, and they exhibit superior properties in several hydrocarbon conversion reactions. Mesoporous means here materials having pores of 2-15 nm and their pore system is regular.

The mesoporous molecular sieve embedded with (in) a zeolite comprises a mesoporous molecular sieve selected from M4IS group, which comprises mesoporous materials with ordered pore system. Preferably the mesoporous molecular sieve is selected from mesoporous alumino-silicates known as the MCM-41 group.

The mesoporous molecular sieve is embedded with a zeolite selected from medium pore zeolites, which are 10-member ring zeolites like MFI, MTT, TON, AEF, MWW and FER structures, and large pore zeolites, which are 12-member ring zeolites like BEA, FAU and MOR structures. Examples of said zeolite groups are ZSM-5, ZSM23, ZSM-22, SAPO-1 I, MCM-22, ferrierite, beta, Y- and X-zeolites and mordenite. Preferably the zeolite is an MFI, MTT, AEF or BEA zeolite.

The catalytic material contains 0.01-10 wt-% aluminium.

A catalyst, which is particularly suitable for the present use, comprises the mesoporous molecular sieve embedded in a zeolite according to the invention and also a carrier or support selected from alumina, silica, clay and any other carriers, in particular metal oxide supports, according to the state of the art, and combinations thereof. Preferably the carrier comprises alumina or silica. The amount of the carrier varies between 10 and 90 wt-%, calculated on the total weight of the catalyst.

The novel group of catalytic materials having a mesoporous molecular sieve embedded in a zeolite structure according to the invention exhibits high specific surface area (BET) which is in the range of 1400 to 500 m$^2$/g, preferably 1200 to 600 m$^2$/g.

The X-ray powder diffraction pattern of the catalytic material according to the invention demonstrates the mesoporous molecular sieve and zeolite structures. The unit cell dimension of the zeolite depends on the amount of Al in the catalytic material. The unit cell size decreases with the amount of Al, from 1.982 nm in a catalytic material containing 0.2 wt-% of Al to 1.972 nm in a catalytic material containing 3.9 wt-% of Al, when the zeolite type was MFI (the code of the material is here MMS). The change in the unit cell size is opposite to the changes observed in zeolites in general. The unit cell sizes were 1.428 nm and 1.430 nm, when the zeolite type was BEA (the code of the material is MMBE).

The $d_{100}$ spacing in the mesoporous molecular sieve MCM-41 decreases with increasing zeolite content. The $d_{100}$ varies from 4.38 nm to 3.81 nm (MM5). The $d_{100}$ varies from 4.09 nm to 3.97 nm (MMBE). The unit cell dimension and the $d_{100}$ values are the same in pure zeolite and MCM-41 phases as in their mechanical mixtures. The changes in the $d_{100}$ spacing and the unit cell dimension are a clear evidence of a true chemical bonding between the mesoporous molecular sieve and the embedded zeolite in the catalytic material according to the invention.

The characteristic features of the novel catalytic material, the mesoporous molecular sieve embedded in a zeolite, was detected and measured by X-ray powder diffraction, scanning electron microscopy, transmission electron microscopy, specific surface area measurement using nitrogen absorption (BET) and acidity measurements using ammonia-TPD and pyridine-FTIR.

The total number of acid sites can be measured by the capacity of the catalytic material to bind strong base molecules, such as ammonia or pyridine. The total acidity was measured by ammonia-temperature programmed desorption (TPD) and Brönsted and Lewis acidity by pyridine-infrared spectroscopy (FTIR). The acidity of the catalytic material can be tailored by the amount of Al introduced in the structure and modifying the aluminium (Al) content in the zeolite, MCM-41 and MM phases.

Since there are no international standard methods available for acidity determination, the methods used are described below.

Acidity determination was performed by $NH_3$-TPD. The total acidity of catalytic materials was measured by temperature-programmed desorption of ammonia ($NH_3$-TPD) using an Altamira AMI-1OO instrument. Sample size was 40 mg. The total acidity was measured by desorption of $NH_3$ as a function of temperature. The acidity of the samples was calculated from the amount of $NH_3$ adsorbed at 200° C. and desorbed between 100° C. and 500° C. The $NH_3$-TPD instrument was equipped with a thermal conductivity detector (TCD) manufactured by Gow Mac. A ramp rate of 20° C./min was applied and the temperature was linearly raised to 500° C. where it was held for 30 min. The quantification was made using pulses of known volume of 10% $NH_3$ in He.

Acidity determination was determined also by pyridine-FTIR. The acidity of samples was measured by infrared spectroscopy (ATI Mattson FTIR) by using pyridine (99.5%, a.r.) as a probe molecule for qualitative and quantitative determination of both Brönsted and Lewis acid sites. The samples were pressed into thin self-supported wafers (10 to 12 mg/cm$^2$). Pyridine was first adsorbed for 30 mm at 100° C. and then desorbed by evacuation at different temperatures (250, 300 and 450° C., respectively) to obtain a distribution of acid site strengths. All spectra were recorded at 100° C. with a spectral resolution equal to 2 cm$^{-1}$. Spectral bands at 1545 cm$^{-1}$ and 1450 cm$^{-1}$, respectively, were used for identifying Bronsted (BAS) and Lewis acid sites (LAS). The amounts of BAS and LAS were calculated from the intensities of corresponding spectral bands by using the molar extinction coefficients.

The acid sites are situated on the surface of the catalytic material. The total surface area and pore volume were evaluated using $N_2$-adsorption and desorption. The average mesopore surface area and mesopore diameter were evaluated from the $N_2$-desorption utilizing the BJH (Barrer-Joyner-Halenda) equation. The pore diameter has a size-limiting effect both on reactants and products. The size of the micropores depend on the structure of the zeolite; pores with a diameter less than 2 nm are defined as micropores and pores with a diameter between 2 and 50 nm are defined as mesopores according to IUPAC.

The surface area and total pore volume decrease when the zeolite is embedded in the mesoporous molecular sieve as can be seen from Table I below, presenting surface area, pore volume and pore diameter values for MMS and MMBE, and for comparison MCM-41, MFI and BEA data are enclosed.

TABLE 1

| Surface area and porosity | BET area (m$^2$/g) | BJIH mesopore area (m$^2$/g) | Total pore volume (cm$^3$/g) | BJH pore diameter (nm) |
|---|---|---|---|---|
| Na-MCM-41-20 | 949 | 947 | 0.829 | 2.6 |
| Na-MM5-2Z5 | 896 | 1145 | 0.814 | 2.5 |
| Na-MMS-4Z5 | 820 | 1009 | 0.713 | 2.6 |
| Na-MMS-4Z5-2Al | 867 | 1069 | 0.794 | 2.5 |
| Na-MM5-4Z5-2Al25 | 733 | 599 | 0.656 | 2.4 |
| MFI ZSM-5 | 360 | 100 | 0.351 | 20* |
| Na-MMBE-4B | 879 | 884 | 0.692 | 2.7 |
| Na-MMBE-4B-2Al | 844 | 859 | 0.742 | 2.7 |
| Na-MMBE-413-2Al35 | 793 | 684 | 0.835 | 2.6 |
| BEA | 585 | 85 | 0.254 | None |

*=interparticle void size

The method for the manufacture of the mesoporous molecular sieve embedded with or in a zeolite comprises the steps of:
 a) preparing of zeolite nuclei from a silicon source and an aluminium source and structure directing agent (template R), or a silicate or aluminosilicate precursor for the zeolite nuclei, and optionally removing the template with a step calcination procedure;
 b) preparing of mesoporous molecular sieve gel mixture from a silicon source,
   i. an optional aluminium source, and surfactant (S);
   ii. introducing the zeolite nuclei or the silicate or aluminosilicate precursor, prepared in step a) as reagents to the mesoporous molecular sieve gel mixture obtained in step b), and the zeolite nuclei or the silicate or aluminosilicate precursor are homogenised and dispersed in the molecular sieve gel;
 c) performing gel ripening of the mixture of step c) under stirring;
 d) carrying out hydrothermal synthesis of the mixture of step c) by maintaining the mixture under sufficient conditions including a temperature of from about
 e) 100° C. to about 200° C. under static or dynamic mode of stirring until crystals are formed;
 f) recovering the crystals;
 g) washing of the solid product;
 h) drying of the solid product, and
 i) removing the surfactant (S) partly or totally with a step calcination procedure and optionally the template (R) if it was not removed in step a), whereby a mesoporous molecular sieve embedded with a zeolite catalyst is obtained.

In step a) the zeolite nuclei are prepared from a silicon source and an aluminium source and structure directing agent (template R). The silicon source is selected from silicon oxides, preferably from colloidal silica, solid silica and fumed silica.

The aluminium source is selected from aluminium sulphate ($Al_2(SO_4)_3.18H_2O$), hydrated aluminium hydroxides, aluminates, aluminium isoproxide and alumina.

A suitable template is selected in order to obtain the desired zeolite structure. Examples of typically used templates are alkyl ammonium hydroxides, alkyl ammonium halogenides, alkyl amine hydroxide and alkyl amine halogenides like tetrapropylammonium bromide, tetramethyl ammonium hydroxide, tetramethylammonium bromide, tetraethylammonium bromide, tetraethylammonium hydroxide, piperidine, pyrrolidine, octylamine, ethylenediamine, 1,6-diaminohexane and hexamethyleneimine.

The temperature in step a) is between 40 and 200° C. and the preparation can take place in static or in dynamic mode. Finally, in step a) the template is optionally removed by a thermal treatment procedure known as step calcination procedure. The temperature of the treatment is in the range of from 350 to 900° C. The template may alternatively be removed in step i) if it was not removed in step a) but preferably the template is removed in step a).

In step b), the mesoporous molecular sieve gel is prepared from silicon sources, optional aluminium sources, and surfactant. In step c), the zeolite nuclei or the silicate or alumino silicate precursor prepared in step a) is introduced into the molecular sieve gel under stirring. The formed mixture is homogenized and the zeolite nuclei or the silicate or aluminosilicate precursor is dispersed. For adjusting the acidity of the product, an additional aluminum source can be added. The stirring rate in step c) ranges from 50 to 1000 rpm, the treatment time is 10 to 500 minutes.

In the following steps, the gel obtained is ripened under stirring, subjected to hydrothermal synthesis at 100 to 200° C., crystals are recovered for example filtration and the solid product thus isolated is thoroughly washed with water. The product is then dried and the surfactant is removed by thermal treatment, e.g. by calcinations at a temperature of 350 to 900° C. Further details of the manufacturing process are disclosed in FI Patent Application No. 20041675.

A catalyst of the above kind can be used in the dimerization step. The catalyst is, for example placed in a packed bed. The temperature of the reaction zone is typically 50-200° C., preferably 80-150° C. The upper level of the temperature range is set by avoiding unwanted side reactions. The WHSV is about 2 to 200 $h^{-1}$.

The effluent from the reaction zone is conducted to a separation zone, where components are separated from one another. The composition of the product flow depends on the process parameters and on the composition of the feed. As already discussed, the process of the present invention can be used for producing dimerized product from olefinic feedstock. The olefins present in the feed can be either $C_3$-olefins, $C_4$-olefins, $C_5$-olefins or a mixture of these. Thus it is clear that the composition of the product flow depends essentially on the fraction used as the feedstock.

According to the first preferred embodiment, $C_4$-olefins are dimerized. The compositions of the feed have already been discussed, and product compositions then are as follows:

The dimer fraction of the reaction product for a feed comprising (among other, less reactive compounds) both $C_4$- and $C_5$-isoolefins (in a ratio 45:55) includes trimethylpentenes 20-30 wt-%, in particular 25-28 wt-%, tetramethylpentenes and trimethylhexenes 20-30 wt-%, in particular 20-25 wt-%, tetramethylhexenes 4-8 wt-%, in particular 5-6 wt-%, and trimethylheptenes 2-5 wt-%, in particular 3-4 wt-%. The rest of the dimer product is less branched olefins.

According to an embodiment, a part of the first product, which is not recycled, is transferred to alkylation.

According to an embodiment, the second product is subjected to hydrogenation to provide a partly or totally hydrogenated product. It should, however, be pointed out that even the unhydrogenated product is acceptable and even advantageous as a fuel component.

FIG. 1 shows the simplified process configuration of a dimerization process according to the invention.

According to the embodiment shown in the figure, the process comprises a reaction zone 1 and a separation zone 2. Further, upstream of the reaction zone 1 there is a selective hydrogenation zone 3 and a dehydration zone 4, preferably connected in series, as shown in FIG. 1. The effluent of the dehydration zone 4 is conducted to a stripper 5, from which light components, such as hydrogen and evaporated water are removed in gas phase while the remaining liquid effluent is conducted to the reaction zone 1.

The dimerization product is formed in reaction zone 1 and the dimers are separated from unreacted components in separation zone 2, as shown. The unreacted components are circulated in flow 6. The inert components and the leave the process in flow 7.

The reaction zone comprises one or several reactors. Many reactors of a continuous type capable of housing a solid catalyst and a liquid reagent are suitable for the invention. According to an embodiment of the invention, the reactor must allow regeneration of the catalyst. The regeneration can be done during continuous process operation. Alternatively, two or several reactors can be used in parallel, this allows regenerating one reactor when other is being operated.

A typical dimerization system consists of one or more reaction sections followed by product separation and arrangements for recycling of the unreacted reactants. Several reaction and product separation stages may be connected in series if conversion requirement is high.

The reaction zone comprises any reactor type suitable for liquid phase operation and in which a solid catalyst can be used. These reactor types include a fixed bed reactor, a moving bed reactor, a mixing tank reactor, a fluidized bed reactor, or a spouted bed reactor or a combination of these reactors.

In order to meet the requirements for continuous operation, the dimerization catalyst must be regenerated regularly. It is often necessary to include facilities for catalyst regeneration in the reactor system. If continuous operation is not imperative, it is of course possible to pause process operation for catalyst regeneration. However, in industrial operation it is preferred to have several reactors that can be regenerated one at a time, while the others are in production. An example of such arrangement according to our invention is two or more fixed bed reactors connected in such a manner that each of them can be separated from the process for changing or regenerating the catalyst.

Another preferred option in dimerization operations is to use a reactor from which the catalyst can be extracted continuously for regeneration. In an embodiment of our invention, a fluidized bed or spouted bed reactor is used, from which the catalyst can be extracted continuously and recycled through a regeneration facility.

According to a preferred embodiment of the invention, the separation zone comprises a distillation column. The product flow from the reaction zone comprises light hydrocarbons remaining from the hydrocarbon feed, and oligomers formed in the reactor having a boiling point substantially higher than that of the feed. This makes separation by distillation simple.

According to an embodiment of our invention, the separation zone is preferably a distillation zone. The reactants are monomers and the product is a mixture of oligomers and thus they have significantly different boiling points making separation by distillation easy. Considering the ease of separation, a flash drum, evaporator, stripper, or fractionator and other distillation devices known in the art can be used.

In another preferred embodiment of the invention the reaction zone comprises two reactors in parallel, used in turn. This means that when one reactor is being regenerated, the other reactor is used for the dimerization. The separation zone comprises a distillation column. A part of the feed is withdrawn from the process and the other part is directed back to the separation zone in order to raise the yield of the reaction zone.

The reactor can be a fluidized bed reactor and the catalyst is continuously regenerated in a regenerator unit.

As discussed above, the step of contacting the $C_4$ to $C_6$ isoolefins at conditions conducive to dimerization with the catalytic material, is preferably carried out essentially in the absence of butadiene and water in the feedstock. Thus, the feedstock should contain less than 1000 ppm of butadiene and less than 100 ppm of water, the concentrations of butadiene and water being calculated from the weight of the feedstock. It is particularly preferred that the feedstock contains less than 500 ppm of butadiene calculated from the weight of the feedstock. Similarly, it is preferred that the feedstock is essentially free from other compounds containing two or more double carbon-to-carbon bonds or at least one triple carbon-to-carbon bonds. Examples of such compounds include isoprene, acetylene and other compounds with fused or conjugated double bonds or containing at least one trip bond (carbon-to-carbon). Preferably there is less than 500 ppm, in particular less than 100 ppm, preferably less than 50 ppm and suitably less than 30 ppm of said compounds with two or more double carbon-to-carbon bonds or at least one triple carbon-to-carbon bond. In a preferred embodiment, the aforementioned limits refer to the total concentration of butadiene and other compounds containing two or more double carbon-to-carbon bonds potentially along with compounds containing at least one triple carbon-to-carbon bond.

It is also important that the feedstock is essentially free from polar compounds. For that purpose, the feedstock is, according to one embodiment, subjected to selective hydrogenation prior to dimerization to remove unsaturated hydrocarbon compounds containing triple bonds or more than two double bonds. Preferably, the feedstock is subjected to dehydration prior to dimerization. Just like with water, there is preferably less than 100 ppm, in particular less than 50 ppm, suitably less than 30 ppm or even less than 10 ppm of polar compounds, such as polar organic compounds, present in the feed. In a preferred embodiment, the aforementioned limits refer to the total amount of water and other polar compounds.

Based on the above, as an example of a particularly preferred embodiment, the following can be mentioned:

A process for producing dimers, which optionally after hydrogenation, are useful as automotive gasolines or components thereof, comprising the steps of
  providing an industrial refinery feedstock, which contains $C_4$ to $C_6$ isoolefins,
  subjecting the feedstock to selective hydrogenation in order to reduce the concentration of any unsaturated hydrocarbon compounds containing two or more unsaturated double carbon-to-carbon bonds or at least one triple bond to less than 1000 ppm, in particular less than about 750 ppm, preferably less than about 500 ppm, to provide a hydrogenated feedstock,
  feeding the hydrogenated feedstock to dehydration in order to reduce the concentration of water to less than 10 ppm, calculated from the weight of the feedstock, to provide a hydrogenated and dehydrated feedstock, and
  conducting the hydrogenated and dehydrated feedstock to dimerization.

The selective hydrogenation, meaning a hydrogenation which will specifically hydrogenate unsaturated compounds except for the desired starting material of the dimerisation process, i.e. the isoolefins or linear olefins, in particular isobutylene, is carried out in the presence of an excess of hydrogen, free hydrogen being removed after the hydrogenation step in a stripper. The free hydrogen is removed together with any water recovered from the dehydration step in a stripper. From the stripper, a liquid effluent is recovered and subjected to dimerization.

The following non-limiting examples illustrate the invention:

EXAMPLE 1

Synthesis of Mesoporous Molecular Sieve Embedded in MIFI Structure, NaMMS-96h-4Z5-2A1-35, Using an Aluminium Source EXAMPLE 1a Synthesis of Na-MMS-96h-4ZS-2A1-35

The synthesis of Na-MM5-96h-4ZS-2A1-35 was carried out by preparing solutions A, B and C. Solution A was prepared by mixing 4.5 g of fumed silica with 51.7 g of distilled water with continuous stirring (196 rpm) for 20 minutes. Solution B was prepared by adding 18.1 g of tetramethylammonium silicate to 11.7 g sodium silicate with continuous stirring (180 rpm) and the obtained mixture was stirred for 20 minutes. Solution C was prepared by dissolving 26.3 g of tetradecyl trimethyl ammonium bromide in 174.3 g of distilled water with vigorous stirring (336 rpm) for 20 minutes. Solution B was added to Solution A slowly (in 15 mm) with vigorous stirring (320 rpm) and after the addition of Solution B the obtained mixture was stirred for further 20 mm. Solution C was added to the mixture (A+B) slowly (20 mm) with vigorous stirring (336 rpm) and after the addition of solution C the mixture was further stirred for 20 minutes. Then 4.2 g of MFI nuclei, prepared as described in Example 6 of F120041664, were dispersed in the gel mixture (A+B+C) under vigorous stirring (340 rpm) for 20 minutes. The homogenisation of the dispersed MFJ was carried out by further vigorous stirring (340 rpm) of the gel for 35 minutes. Then 2.3 g of aluminium isopropoxide was added to the mixture and stirred for 20 min. Then the gel was allowed to ripen for three hours with stirring (180 rpm). pH of the gel was controlled and the gel was introduced in a teflon cup which was then inserted in an autoclave. The synthesis was carried out for 96 h at 100° C. After completion of the synthesis, the reactor was quenched and the obtained mesoporous material was filtered and washed thoroughly with distilled with water. The obtained Na-MM5-96h-4Z5-2A1-35 was dried and calcined using step calcination procedure in a muffle oven at 450° C.

EXAMPLE 1b

Preparation of H-MM5-96 h-4ZS-2A1-35

A composition comprising 10 g of Na-MMS-96h-4ZS-2A1-35 (manufactured above) was ion-exchanged with 1 M ammonium nitrate aqueous solution for 24 h at room temperature. After the ionexchange the mesoporous material was washed thoroughly, dried and calcined using step calcination procedure in a muffle oven at 450° C.

The following examples illustrate the influence of butadiene and water on the activity of a mesoporous catalyst (H-MM5-96h-4ZS-2A1-35) according to Finnish Patent Application No. 20041675. The examples include dimerization tests carried out with isobutylene in a microreactor at a pressure of 20 bar. The catalyst was packed into the reactor in the form of a powder and mixed with silicon carbide (SiC). The concentration of isobutylene in the dried (anhydrous) feed was about 20 wt % in Examples 1, 3 and 4. In Examples 2, 5, 6, 7 and 9, the concentration of isobutylene in the industrial feed was about 17 wt-% while the concentration of 1-butylene was of about 15 wt-%.

EXAMPLE 2

Figure 2:
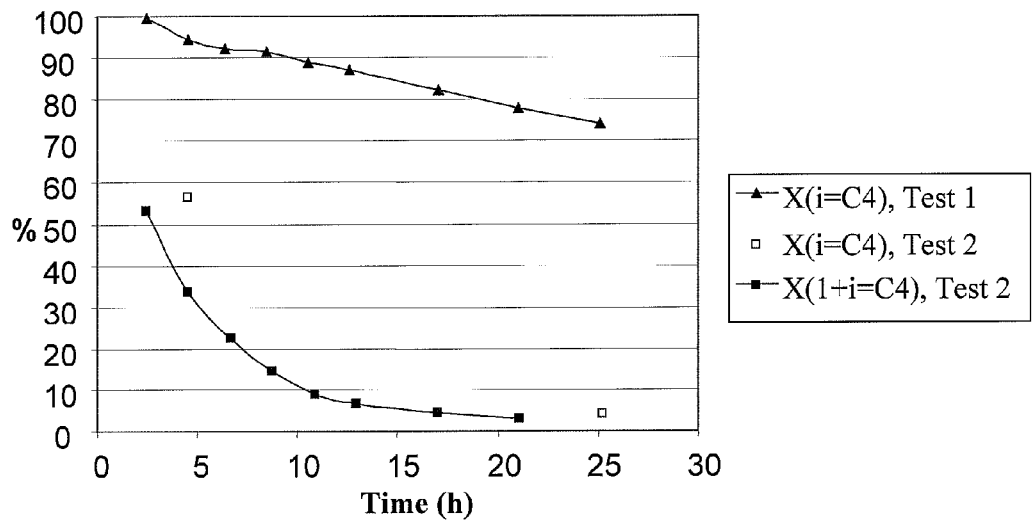
FIG. 2 shows in graphical form the influence of feed composition on catalyst activity based on the results in Example 2 (Tests 1 and 2)

The Influence of the Composition of the Feed on the Activity of the Catalyst The influence of the feed composition on the activity of the catalyst was studied by means of Tests 1 and 2, the results of which are presented in Table 1 and FIG. 2. The tests were carried out at a temperature of 80° C. at a WHSV of 80 h$^{-1}$ and the feed of Test 1 was dry. The concentration of the inert n-pentane was about 80%. In Test 2 an industrial refinery C$_4$-hydrocarbon feed was used, in which the isobutylene concentration was about 17 wt-%. The industrial feed contained isobutylene and in addition to alkanes also other alkenes such as 1- and 2-butylene, and small amounts of butadiene and water.

When the results are examined the influence on the feed composition on the activity can clearly be seen. The conversion of isobutylene decreases much faster when an industrial refinery feed is being used. Based on the result we have to our surprise found that water and butadiene have apparently deactivated strongly.

TABLE 2

Conversion of isobutylene X(i = C4) in Tests 1 and 2 and the conversion of 1 + i-butylene X(1 + i = C4) in Test 2.

| Test 1 | | Test 2 | | |
| --- | --- | --- | --- | --- |
| Time (h) | X(i = C4) | Time (h) | X(1 + i = C4) | X(i = C4) |
| 2.4 | 99.8 | 2.5 | 53.0 | |
| 4.5 | 94.4 | 4.6 | 33.6 | 56.3 |
| 6.4 | 92.2 | 6.7 | 22.5 | |
| 8.5 | 91.5 | 8.8 | 14.4 | |
| 10.5 | 89.0 | 10.9 | 8.8 | |
| 12.6 | 87.1 | 13.0 | 6.5 | |
| 17.0 | 82.3 | 17.0 | 4.3 | |
| 21.0 | 77.8 | 21.1 | 2.9 | |
| 25.1 | 74.0 | 25.3 | — | 4.0 |

These results are also shown in FIG. 1. As will appear, the catalyst was deactivated considerably much faster in Test 2 wherein the feed contained, i.a. butadiene and water.

EXAMPLE 3

The Catalyst-Deactivating Effect of Butadiene

Figure 3:
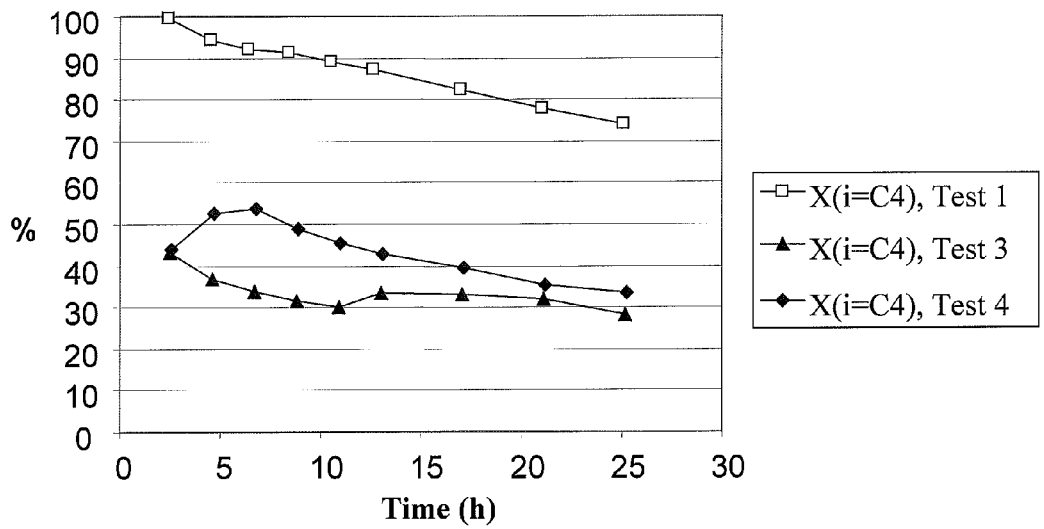
FIG. 3 shows in graphical form the influence of butadiene on catalyst activity based on the results in Example 3 (Tests 3 and 4)

Table 3 and FIG. 3 show the conversion of isobutylene in Tests 1, 3 and 4. The tests were carried out at a temperature of 80° C. and at a WHSV value of 80 h$^{-1}$, no dehydration of the feed being carried out. In both Tests 3 and 4 similar feeds were used which differed from the one used in Test 1 only as far as the concentration of the butadiene is concerned. The concentration of butadiene in Test 1 was about 0.0 wt % and in Tests 3 and 4 the feed used contained about 0.5 wt % of butadiene. The feed of Tests 3 and 4 was prepared from the feed of Test 1 by adding butadiene. Based on the results of the tests, we conclude that butadiene present in the feed deactivates very strongly the catalyst. The influence of butadiene on the activity of the catalyst was, based on our tests, extremely fast, after about 2.5 h from the start of the test, the deactivation of the catalyst is substantially no longer dependent on the concentration of the butadiene in the feed.

TABLE 3

The influence of butadiene on the activity of the catalyst.

| Test 1 | | Test 3 | | Test 4 | |
| --- | --- | --- | --- | --- | --- |
| Time (h) | X(i = C4) | Time (h) | X(i = C4) | Time (h) | X(i = C4) |
| 2.4 | 99.8 | 2.5 | 43.3 | 2.6 | 44.0 |
| 4.5 | 94.4 | 4.6 | 37 | 4.7 | 52.6 |
| 6.4 | 92.2 | 6.7 | 33.7 | 6.8 | 53.8 |
| 8.5 | 91.5 | 8.8 | 31.5 | 8.9 | 48.9 |
| 10.5 | 89.0 | 10.9 | 30.2 | 11.0 | 45.3 |
| 12.6 | 87.1 | 13.0 | 33.3 | 13.1 | 42.9 |
| 17.0 | 82.3 | 17.1 | 33.3 | 17.2 | 39.5 |
| 21.0 | 77.8 | 21.1 | 32.0 | 21.2 | 35.3 |
| 25.1 | 74.0 | 25.2 | 28.0 | 25.2 | 33.4 |

EXAMPLE 4(1)

Deactivation of the Catalyst by the Influence of Water (1)

Figure 4:
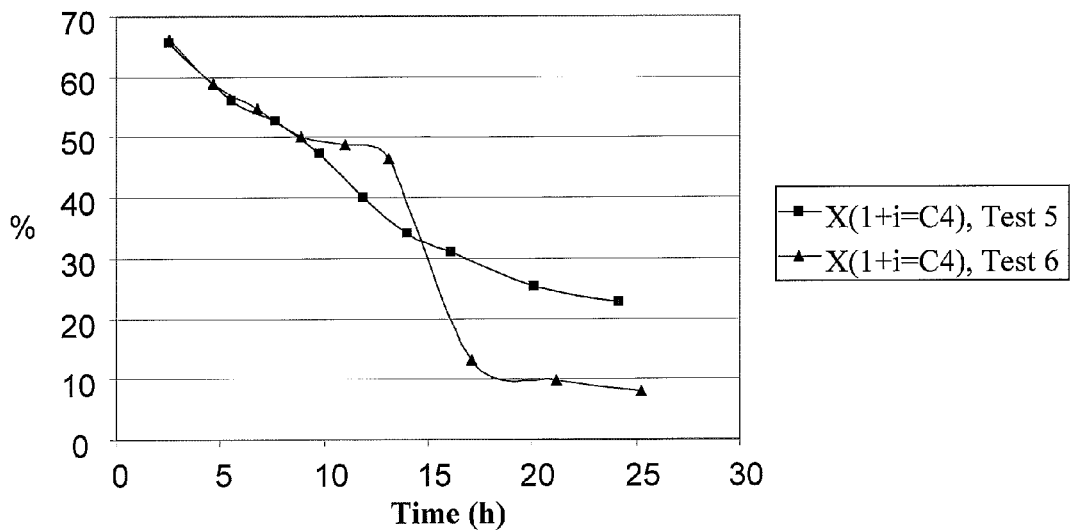
FIG. 4 shows in graphical form the conversion rates of butylenes as a function of time in Tests 5 and 6 of Example 4(a)

Tests 5 and 6 were carried out at a temperature of 100° C. at a WHSV value of 40 h$^{-1}$ (FIG. 4, Table 4). The feed was conducted into the reactor through a dehydration unit which contained about 40 ml of a 3 A molecular sieve. In Test 5, the dehydration was in operation during the whole duration of the test. In Test 6 the dehydration medium was exchanged for another regenerated dehydration medium of the same kind after 8.9 h after the taking of a fourth GC sample. After 13.1 hours the dehydration unit was taken completely out of operation. The results show that an enhancement of the dehydration efficiency clearly slowed up deactivation, whereas the termination of feed dehydration during test caused a collapse of catalyst activity. Any water present in the feed has, therefore, an extremely strong deactivating influence on catalyst activity.

TABLE 4

Conversion of 1 + i-butylene in Tests 5 and 6.

| Test 5 | | Test 6 | |
| --- | --- | --- | --- |
| Time (h) | X(1 + i = C4) | Time (h) | X(1 + i = C4) |
| 2.6 | 65.5 | 2.5 | 66.2 |
| 5.6 | 56.1 | 4.7 | 59.0 |
| 7.7 | 52.8 | 6.8 | 54.8 |
| 9.8 | 47.4 | 8.9 | 50.0 |
| 11.9 | 40.0 | 11.0 | 48.7 |
| 14 | 34.2 | 13.1 | 46.4 |
| 16.1 | 31.1 | 17.1 | 13.1 |
| 20.2 | 25.4 | 21.2 | 9.9 |
| 24.2 | 22.7 | 25.2 | 8.1 |

FIG. 3 shows that the activity of Catalyst 6 collapsed after the termination of feed dehydration during the tests.

EXAMPLE 4(2)

Deactivation of the Catalyst by the Influence of Water (2)

Figure 5:
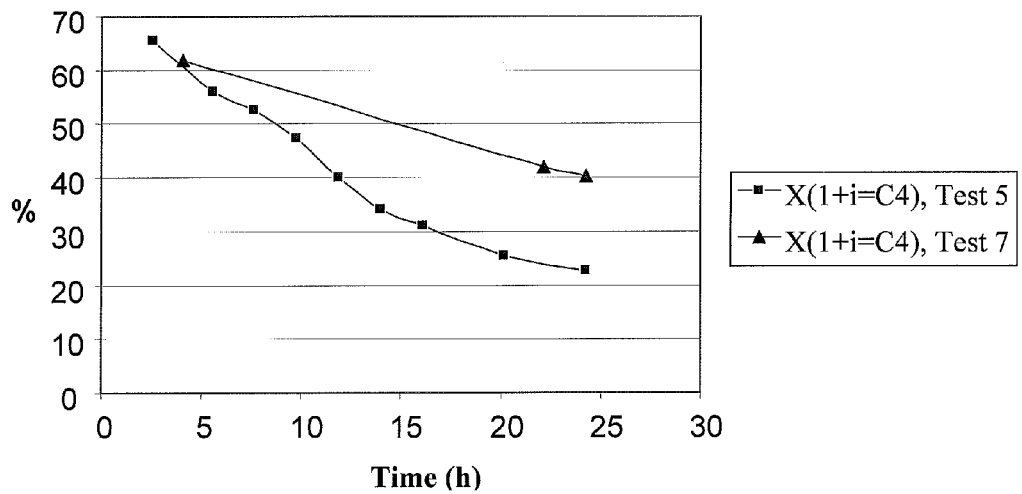
FIG. 5 depicts the influence of feed dehydration on catalyst deactivation rate based on the results of Tests 5 and 7 in Example 4(b)

The conversion of 1+i-butylene in Tests 5 and 7 (100° C., 40 h$^{-1}$) are shown in Table 5 and FIG. 5. The tests differed from each other only in the respect of the volumetric amount of the dehydration medium used (molecular sieve 3A). In Test 7 the dehydration unit contained 395 ml of molecular sieve 3A. As apparent, an enhancement of feed dehydration significantly retarded the deactivation rate of the catalyst. Examples 4(1) and 4(2) clearly show that by dehydration and separation of water the time of operation of the catalyst can be substantially prolonged. In Test 5, the average water concentration was 100 ppm in the reactor feed and in Test 7 the concentration was 10 ppm.

TABLE 5

Conversion of 1 + i-butylene in Tests 5 and 7.

| Test 5 | | Test 7 | |
|---|---|---|---|
| Time (h) | X(1 + i = C4) | Time (h) | X(1 + i = C4) |
| 2.6 | 65.5 | 4.1 | 62.0 |
| 5.6 | 56.1 | 22.2 | 42.1 |
| 7.7 | 52.8 | 24.3 | 40.2 |
| 9.8 | 47.4 | | |
| 11.9 | 40.0 | | |
| 14.0 | 34.2 | | |
| 16.1 | 31.1 | | |
| 20.2 | 25.4 | | |
| 24.2 | 22.7 | | |

EXAMPLE 5

Oxidizing Regeneration of Catalyst

Figure 6:
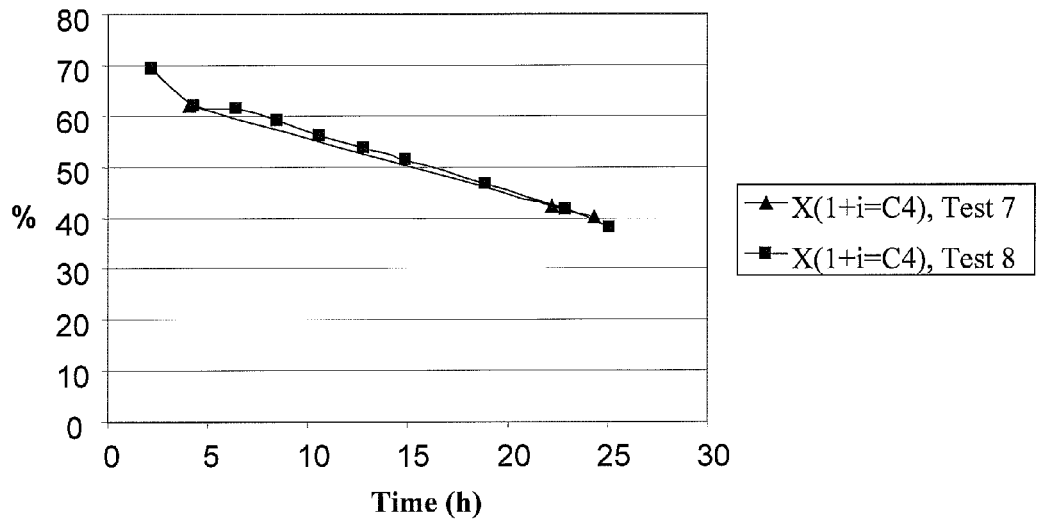
FIG. 6 shows in graphical form catalyst activity after oxidative regeneration based on Tests 7 and 9 in Example 5.

The conversion of 1+i-butylene in Tests 7 and 8 (100° C., WHSV 40 h$^{-1}$) are shown in Table 6 and FIG. 6. Same catalyst packing was used in Test 7, in Test 8 and in an unnumbered test between tests 7 and 8. Catalyst was regenerated by nitrogen (6 h, 450° C.) after test 7 but activity did not return to the same level as it was in Test 7. The catalyst was tested (unnumbered test) during about 25 hours (100° C., WHSV 40 h$^{-1}$) after regeneration with nitrogen, and the catalyst was regenerated by an oxidative method after the unnumbered testing. The oxidizing gas did not contain oxygen over 5 volume percent and the temperature of the catalyst was over 450° C. for about 6 hours. The results show that the activity of catalyst can be easily returned by oxidative regeneration.

TABLE 6

Conversion of 1 + i-butylene in Tests 7 and 8

| Test 7 | | Test 8 | |
|---|---|---|---|
| Time (h) | X(1 + i = C4) | Time (h) | X(1 + i = C4) |
| 4.1 | 62 | 2.2 | 69.3 |
| 22.2 | 42.1 | 4.3 | 61.9 |
| 24.30 | 40.2 | 6.40 | 61.4 |
| | | 8.50 | 59 |
| | | 10.6 | 56.2 |
| | | 12.8 | 53.8 |
| | | 14.9 | 51.5 |
| | | 18.9 | 46.5 |
| | | 22.9 | 41.6 |
| | | 25.1 | 38.3 |

The invention claimed is:

1. A process for dimerizing olefins in the presence of a catalyst, wherein a hydrocarbon feedstock containing $C_4$ to $C_6$ isoolefins is subjected to dimerization, said process comprising the steps of Contacting, in at least one reaction zone, the $C_4$ to $C_6$ isoolefins at conditions conducive to dimerization with a catalytic material comprising an acidic mesoporous molecular sieve embedded with a zeolite, the catalytic material being thermally stable at a temperature of at least 900° C., wherein said acidic mesoporous molecular sieve embedded with a zeolite is produced by preparing a mesoporous molecular sieve gel mixture, introducing a zeolite nuclei and homogenizing and dispersing said zeolite nuclei in said molecular sieve, and carrying out the contacting step essentially in the absence of butadiene and water in the feedstock.

2. The process according to claim 1, wherein the feedstock contains less than 1000 ppm of butadiene, the concentration of butadiene being calculated from the weight of the feedstock.

3. The process according to claim 1, wherein the feedstock contains less than 100 ppm of water, the concentration of water being calculated from the weight of the feedstock.

4. The process according to claim 1, wherein the feedstock contains less than 500 ppm of butadiene and less than 30 ppm of water, calculated from the weight of the feedstock.

5. The process according to claim 1, wherein the feedstock is essentially free from compounds containing two or more double carbon-to-carbon bonds or at least one triple carbon-to-carbon bonds.

6. The process according to claim 1, wherein the feedstock is essentially free from polar compounds.

7. The process according to claim 1, wherein the feedstock is subjected to selective hydrogenation prior to dimerization to remove unsaturated hydrocarbon compounds containing triple bonds or more than two double bonds.

8. The process according to claim 1, wherein the feedstock is subjected to dehydration prior to dimerization.

9. The process according to claim 1, further comprising
providing an industrial refinery feedstock, which contains $C_4$ to $C_6$ isoolefins,
subjecting the feedstock to selective hydrogenation in order to reduce the concentration of any unsaturated hydrocarbon compounds containing two or more unsaturated double carbon-to-carbon bonds or at least one triple bond to less than 1000 ppm by weight to provide a hydrogenated feedstock,
feeding the hydrogenated feedstock to dehydration in order to reduce the concentration of water to less than 100 ppm, calculated from the weight of the feedstock, to provide a hydrogenated and dehydrated feedstock, and
conducting the hydrogenated and dehydrated feedstock to dimerization.

10. The process according to claim 9, wherein the selective hydrogenation is carried out in the presence of an excess of hydrogen, free hydrogen being removed after the hydrogenation step in a stripper.

11. The process according to claim 10, wherein the free hydrogen is removed together with any water recovered from the dehydration step in a stripper.

12. The process according to claim 11, wherein liquid effluent of the stripper is recovered and subjected to dimerization.

13. The process according to claim 1 or 9, wherein dimerization is being carried out at a temperature of 50 to 200° C.

14. The process according to claim 13, wherein dimerization is carried out at a temperature of 80 to 150° C.

15. The process according to claim 1 or 9, wherein the pressure of the reaction zone is maintained above the vapour pressure of the mixture present in the reactors.

16. The process according to claim 15, wherein the pressure of the reaction zone is maintained at 10 to 50 bar.

17. The process according to claim 16, wherein the pressure of the reaction zone is maintained at about 15 to 25 bar.

18. The process according to claim 1, wherein the catalytic material has a specific surface area in the range of from 1,400 to 500 m²/g.

19. The process according to claim 1, wherein the catalytic material comprises a mesoporous molecular sieve selected from the M41S group.

20. The process according to claim 1, wherein the catalytic material comprises a medium pore zeolite selected from the group of MFI, mu, TON, AEF and FER zeolites and large pore zeolites comprising BEA, FAU and MOR zeolites.

21. The process according to claim 19 or 20, wherein the mesoporous molecular sieve is MCM-41 or MCM-48 and the zeolite is an MFI or BEA zeolite.

22. The process according to any of claims 18 to 20, wherein the catalyst is in proton form, cationic form or modified with a metal.

23. The process according to any of claims 18 to 20, wherein the catalyst comprises 90-10 wt-% of the catalytic material according to claim 10 and 10-90 wt-% of a carrier.

24. The process according to claim 18, wherein the catalytic material has a specific surface area in the range of from 1,200 to 600 m²/g.

25. The process according to claim 19, wherein the mesoporous molecular sieve is MCM-41 or MCM-48.

26. The process according to claim 20, wherein the zeolite is selected from the group of MFI, MTT, AEF, BEA and MOR zeolites.

27. The process according to claim 1, further comprising at least one separation zone, wherein the separation zone comprises a distillation zone.

28. The process according to claim 27, wherein the distillation zone produces a first product comprising the distillate of the distillation zone and a second product comprising the bottoms product of the distillation zone.

29. The process according to claim 27, wherein the distillation zone is operated so as to provide a product having vapour pressure of 10-20 kPa (Reid) and a distillation point (90 vol-%, ASTM D86) is equal or less than 180° C.

30. The process according to claim 1, wherein the dimerization process is carried out in a reactive distillation system including at least one reaction zone and at least one distillation zone, said at least one reaction zone including at least one reactor and said at least one distillation zone including at least one distillation column.

31. The process according to claim 1, wherein isooctene is produced from a feed comprising isobutene, and the isooctene is optionally hydrogenated to yield isooctane.

32. A process for dimerizing olefinic, lower hydrocarbons, comprising:
feeding an olefinic hydrocarbon feedstock to a reaction zone, wherein the olefinic hydrocarbon feedstock contains unsaturated hydrocarbons, selected from the group consisting of isobutene, 1-butene, 2-butene, linear $C_5$-olefins and branched $C_5$-olefins;
contacting said olefinic hydrocarbon feedstock in liquid phase with an acid catalyst in the reaction zone, wherein the acid catalyst comprises a mesoporous molecular sieve embedded in a zeolite, the catalytic material being thermally stable at a temperature of at least 900° C.; and
recovering from said reaction zone a product containing dimerized olefins.

33. The process according to claim 1, 9 or 32, wherein the step of contacting said olefinic hydrocarbons of the feedstock with an acid catalyst is conducted substantially in the absence of oxygenates and polar compounds.

34. A process for dimerizing olefins in the presence of a catalyst, wherein a hydrocarbon feedstock containing $C_4$ to $C_6$ isoolefins is subjected to dimerization, said process comprising the steps of
contacting, in at least one reaction zone, the $C_4$ to $C_6$ isoolefins at conditions conducive to dimerization with a catalytic material comprising an acidic mesoporous molecular sieve embedded with a zeolite, the catalytic material being thermally stable at a temperature of at least 900° C., wherein said acidic mesoporous molecular sieve embedded with a zeolite is produced by preparing a mesoporous molecular sieve gel mixture, introducing a zeolite nuclei and homogenizing and dispersing said zeolite nuclei in said molecular sieve, and wherein said catalytic material contains only a single zeolite; and
carrying out the contacting step essentially in the absence of butadiene and water in the feedstock.

* * * * *